US011242185B2

(12) United States Patent
Marantis et al.

(10) Patent No.: US 11,242,185 B2
(45) Date of Patent: *Feb. 8, 2022

(54) EVACUATED BOTTLE SYSTEM

(71) Applicant: CORNERSTONE CM, INC., Poland, OH (US)

(72) Inventors: Michael G. Marantis, Poland, OH (US); Joshua W. Hubbard, New Milford, CT (US); Jonathan P. Richards, Derby, CT (US); Richard A. Ponton, New Milford, CT (US)

(73) Assignee: CSCM Management Company LLC, Poland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/182,709

(22) Filed: Feb. 23, 2021

(65) Prior Publication Data

US 2021/0171266 A1  Jun. 10, 2021

Related U.S. Application Data

(63) Continuation of application No. 16/138,223, filed on Sep. 21, 2018, now Pat. No. 10,961,039, which is a
(Continued)

(51) Int. Cl.
*B65D 81/20* (2006.01)
*A61J 1/14* (2006.01)
(Continued)

(52) U.S. Cl.
CPC ............ *B65D 81/2038* (2013.01); *A61J 1/14* (2013.01); *A61J 1/1406* (2013.01); *A61J 1/1412* (2013.01);
(Continued)

(58) Field of Classification Search
CPC ... B65D 81/2015; B65B 31/04; B65B 31/041; B65B 31/042; B65B 31/047; A61J 1/1418; A61M 1/0001
(Continued)

(56) References Cited

U.S. PATENT DOCUMENTS 1,189,465 A    7/1916   Mayo
2,276,421 A    3/1942   Ross
(Continued)

*Primary Examiner* — Timothy L Maust
(74) *Attorney, Agent, or Firm* — Tucker Ellis LLP

(57) ABSTRACT

An evacuated bottle system including a bottle defining a hollow interior, the bottle having a neck with a rim defining an opening; a cap assembly supported on the bottle, the cap assembly including a funnel having a first portion and a second portion, the first portion being insertable within the interior of the bottle and the second portion engaging a portion of the bottle to support the funnel above the rim, the funnel defining a bore that fluidly communicates with the hollow interior of the bottle; a self-sealing membrane that covers the bore formed by the funnel to selectively seal the hollow interior of the bottle; a cap attachable to the bottle, the cap including a cover portion that extends at least partially over the self-sealing membrane to restrain movement thereof, the cover portion being axially spaced from the self-sealing membrane to define a gap that permits axial movement of the self-sealing membrane to selectively open the bottle to fluid communication outside of the bottle.

18 Claims, 11 Drawing Sheets

Related U.S. Application Data continuation of application No. 15/333,454, filed on Oct. 25, 2016, now Pat. No. 10,106,308, which is a continuation of application No. 14/540,477, filed on Nov. 13, 2014, now Pat. No. 9,517,922, and a continuation of application No. 14/540,443, filed on Nov. 13, 2014, now Pat. No. 9,505,599.

(51) Int. Cl.
| | | |
|---|---|---|
| *A61M 1/00* | (2006.01) | |
| *B65B 31/00* | (2006.01) | |
| *B65B 55/10* | (2006.01) | |
| *B67C 11/02* | (2006.01) | |
| *B67C 11/00* | (2006.01) | |

(52) U.S. Cl.
CPC .......... *A61J 1/1418* (2015.05); *A61M 1/0001* (2013.01); *A61M 1/0003* (2013.01); *A61M 1/0011* (2013.01); *B65B 31/00* (2013.01); *B65B 55/10* (2013.01); *B65D 81/20* (2013.01); *B67C 11/02* (2013.01); *B67C 2011/20* (2013.01)

(58) Field of Classification Search
USPC ........................................................ 141/8, 65
See application file for complete search history.

(56) References Cited

U.S. PATENT DOCUMENTS

| | | | |
|---|---|---|---|
| 2,911,123 A | 11/1959 | Saccomanno | |
| 3,088,615 A | 5/1963 | Mumford et al. | |
| D217,850 S | 6/1970 | Lawton et al. | |
| 3,965,902 A | 6/1976 | Reilly et al. | |
| 4,376,439 A | 3/1983 | Lauterjung | |
| 4,763,803 A | 8/1988 | Schneider | |
| 4,889,250 A | 12/1989 | Beyer | |
| 5,031,785 A | 7/1991 | Lemme | |
| 5,188,622 A | 2/1993 | Muller et al. | |
| 5,207,339 A | 5/1993 | Shyu | |
| 5,322,094 A | 6/1994 | Janesko | |
| 5,465,857 A * | 11/1995 | Yang | B65B 31/047 137/522 |
| 5,535,900 A | 7/1996 | Huang | |
| 5,895,383 A | 4/1999 | Niedospial, Jr. | |
| 5,902,298 A | 5/1999 | Niedospial, Jr. et al. | |
| 5,921,419 A | 7/1999 | Niedospial, Jr. et al. | |
| 5,960,837 A | 10/1999 | Cude | |
| 5,971,181 A | 10/1999 | Niedospial, Jr. et al. | |
| 6,199,297 B1 | 3/2001 | Wisniewski | |
| D472,471 S | 4/2003 | McClure et al. | |
| 6,637,321 B2 | 10/2003 | Wang | |
| 6,651,834 B2 | 11/2003 | Wong | |
| D489,992 S | 5/2004 | Brauner et al. | |
| D520,363 S | 5/2006 | Perez | |
| 7,048,724 B2 | 5/2006 | Grossman et al. | |
| 7,086,427 B2 | 8/2006 | Bonich | |
| 7,153,294 B1 | 12/2006 | Farrow | |
| 7,395,942 B2 | 7/2008 | Michalopoulos | |
| D620,362 S | 7/2010 | Boukobza | |
| 7,799,009 B2 | 9/2010 | Niedospial et al. | |
| D673,854 S | 1/2013 | James | |
| 8,701,910 B1 | 4/2014 | Michalopoulos | |
| 9,517,922 B2 | 12/2016 | Marantis et al. | |
| 10,017,315 B2 | 7/2018 | Marantis | |
| 10,106,308 B2 | 10/2018 | Marantis et al. | |
| 10,252,851 B2 * | 4/2019 | Marantis | A61M 1/0003 |
| 10,836,556 B2 | 11/2020 | Marantis | |
| 2003/0105448 A1 | 6/2003 | Shiraishi et al. | |
| 2003/0208165 A1 | 11/2003 | Christensen et al. | |
| 2005/0155666 A1* | 7/2005 | Wilson | B65B 3/22 141/65 |
| 2006/0231556 A1 | 10/2006 | Wei | |
| 2010/0043917 A1 | 2/2010 | Kitchener et al. | |
| 2010/0270260 A1 | 10/2010 | Jung | |
| 2010/0298806 A1 | 11/2010 | Yandell | |
| 2011/0126939 A1 | 6/2011 | Luis | |
| 2011/0303670 A1 | 12/2011 | Baker | |
| 2013/0233822 A1 | 9/2013 | Aneas | |
| 2014/0209603 A1 | 7/2014 | Aneas | |
| 2014/0311617 A1 | 10/2014 | Py | |
| 2016/0038373 A1 | 2/2016 | Ohlin | |
| 2019/0380916 A1 | 12/2019 | Shastri et al. | |

* cited by examiner

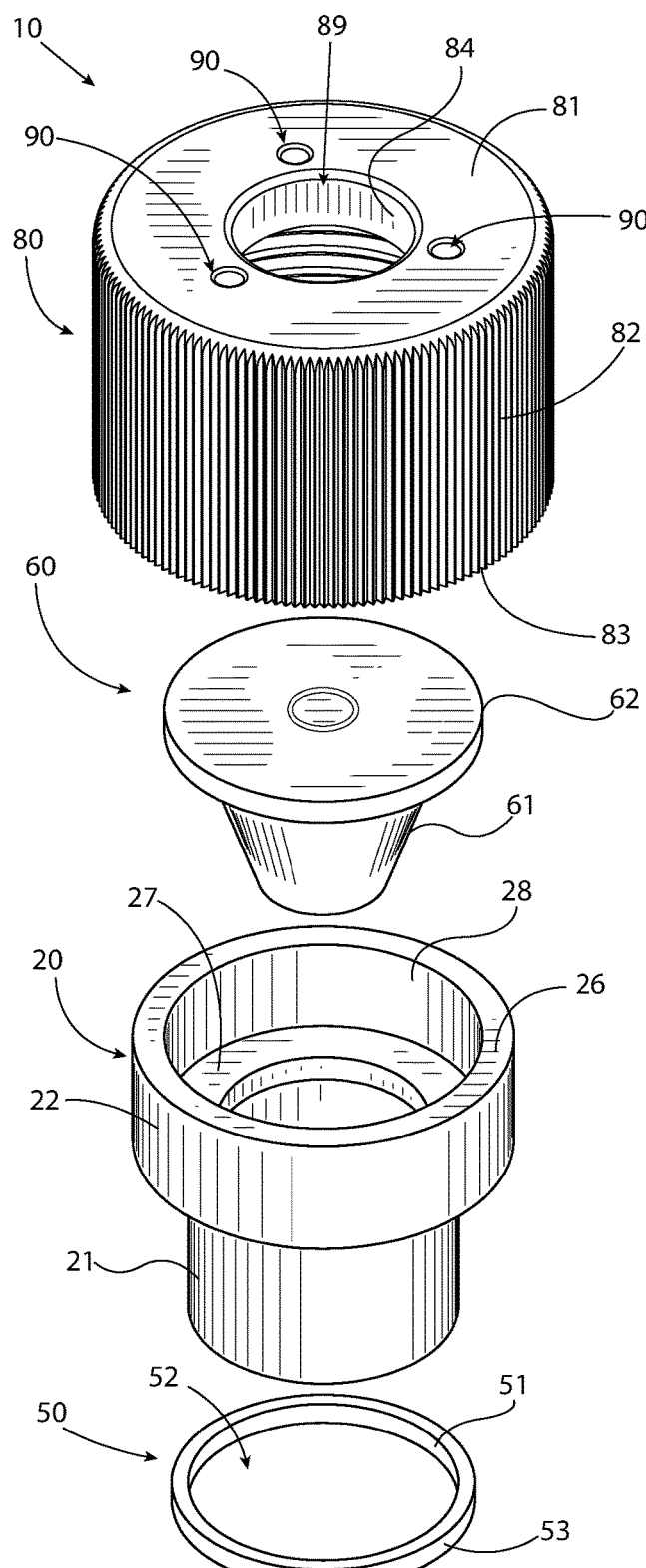
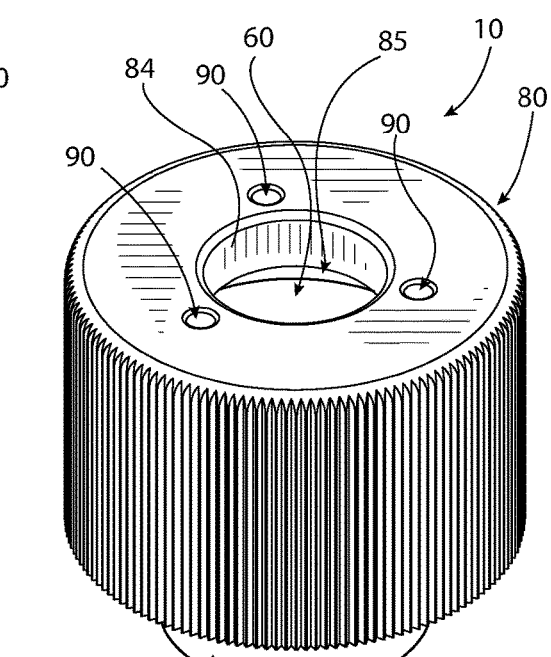
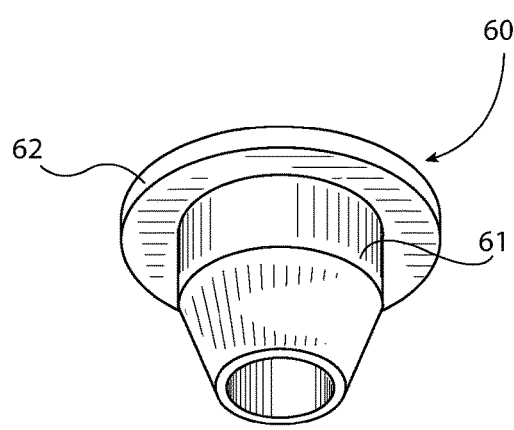
FIG. 1
FIG. 2
FIG. 3

EVACUATED BOTTLE SYSTEM

CROSS-REFERENCE(S) TO RELATED APPLICATIONS

This continuation application claims priority to and the benefit of U.S. application Ser. No. 16/138,223 filed on Sep. 21, 2018, which claims priority to and the benefit of U.S. application Ser. No. 15/333,454 filed on Oct. 25, 2016, which claims priority to and the benefit of U.S. application Ser. No. 14/540,477 filed on Nov. 13, 2014 and U.S. application Ser. No. 14/540,443 filed on Nov. 13, 2014. The entireties of these applications are incorporated herein by reference.

TECHNICAL FIELD

The present invention relates to an evacuated bottle system. More particularly, the present invention relates to an evacuated bottle system that includes a cap assembly that is removably attached to the vacuum bottle and has a membrane covering the opening of the bottle that is exposed externally and seals itself after the membrane is penetrated by a needle, cannula or other tubular instrument, where the self-sealing membrane is displaceable to selectively allow fluid to flow around the membrane to evacuate the bottle.

BACKGROUND OF THE INVENTION

Medical bottles that are used to store fluids that are accessed by inserting a needle through the cap or bottles that contain a vacuum inside that are penetrated by a needle to drain fluid use a permanently attached cap that cannot be removed.

For example, current glass evacuated bottles are used in hospital settings to drain pericardial, peritoneal and pleural fluid from patients with certain conditions. These bottles typically range from 500 to 1000 cubic centimeters in size and are primarily used in radiology. The vacuum inside the bottle is accessed by a needle that is inserted through a membrane held in place by the non-removable top. The non-removable top is typically metal or plastic that is crimped or molded onto the top of the bottle to provide permanent attachment. One drawback of the glass bottles used is that they are considered a safety hazard because of the possibility of breakage during or after a procedure. Also, in terms of disposable, hospitals are required to add a solidifying sand or other substance to liquid medical waste such as the fluid within the bottle. This cannot be accomplished with the current glass bottle and non-removable top. As a result, existing fluids and bottles are disposed of improperly in medical red waste bags or Sharps containers due to the non-removable top.

SUMMARY OF THE INVENTION

The invention generally includes an evacuated bottle system including a bottle defining a hollow interior, the bottle having a neck with a rim defining an opening; a cap assembly supported on the bottle, the cap assembly including a funnel having a first portion and a second portion, the first portion being insertable within the interior of the bottle and the second portion engaging a portion of the bottle to support the funnel above the rim, the funnel defining a bore that fluidly communicates with the hollow interior of the bottle; a self-sealing membrane that covers the bore formed by the funnel to selectively seal the hollow interior of the bottle; a cap attachable to the bottle, the cap including a cover portion that extends at least partially over the self-sealing membrane to restrain movement thereof, the cover portion being axially spaced from the self-sealing membrane to define a gap that permits axial movement of the self-sealing membrane to selectively open the bottle to fluid communication outside of the bottle.

The present invention further provides a cap assembly for an evacuated bottle system, the cap assembly including a funnel having a first portion including a first wall defining a first bore and a second portion; the second portion including a floor extending radially outward from the first portion to form a shoulder adjacent to the first portion; a second wall extending upward from the floor defining a second bore, the first bore and second bore being in fluid communication with each other; a self-sealing membrane having a first portion and a second portion, wherein the first portion includes a tapered end received in the first bore and wherein the second portion is received in the second bore of the funnel and includes a perimeter that extends radially outward of the first portion to overlap at least a portion of the floor; a cap that fits over the second portion of the funnel, the cap defining at least one evacuating opening to which a suction is applied, the cap including a cover portion that extends radially inward over at least a portion of the self-sealing membrane to retain the self-sealing membrane when the suction is applied to the evacuating opening, the cover portion defining a gap above the self-sealing membrane to allow the self-sealing membrane to selectively move axially outward from first bore of funnel to provide fluid communication between the first bore of the funnel and the second bore of the funnel.

The present invention further provides an evacuated bottle system including providing a bottle defining a hollow interior, the bottle having a neck defining an opening that provides fluid communication with the interior; providing a cap assembly including a funnel having a first portion and a second portion, where the second portion extends radially outward from the first portion to form a floor on an interior thereof and a shoulder on an exterior thereof, the first portion defining a first bore and the second portion defining a second bore fluidly connected to the first bore; a self-sealing membrane having a first portion having a tapered end and a second portion that extends radially outward of the first portion, wherein the tapered end is insertable within the first bore of the funnel and the second portion is sized to fit within the second portion of the funnel; and a cap having a cap wall sized to fit over the funnel and a cover portion extending radially inward from the cap wall, the cover portion defining at least one evacuating opening; attaching the cap assembly to the bottle by inserting the first portion of the funnel into the neck of the bottle; supporting the funnel on the neck of the bottle at the shoulder; inserting the tapered end of self-sealing membrane into the first bore where the second portion of the self-sealing membrane covers at least a portion of the floor to seal the first bore of the funnel from the second bore; applying the cap over the funnel and attaching the cap to the bottle, wherein the cover portion extends radially inward over a portion of the self-sealing membrane and defines a gap axially outward of the self-sealing membrane when the tapered end is fully inserted within the first bore; applying a pressure differential relative to the interior of the bottle to create a suction at the evacuating opening to draw the self-sealing membrane axially outward within the gap withdrawing the tapered end from the first bore a distance effective to provide fluid communication between the first bore of the funnel and the second bore the funnel; maintaining the suction until a selected pressure is achieved within the interior of the bottle; and withdrawing the suction, wherein the selected pressure within the bottle draws the tapered end of the self-sealing membrane into the first bore of the funnel to reseal the interior of the bottle.

The present invention also provides a cap assembly for a vacuum bottle that is removably attached to the bottle and includes a membrane that covers the opening defined by the bottle, where the membrane is a self-sealing membrane, and a cap that fits over the membrane to hold it over the opening of the bottle, wherein the cap defines a gap above the membrane that allows it to be displaced away from the bottle to allow fluid to flow out of the bottle to form a vacuum or lower pressure within the bottle.

In accordance with another aspect of the invention, the bottle is constructed of a shatter-proof material. In accordance with another embodiment of the invention, the shatter-proof material is a plastic. In accordance with still another embodiment of the invention, the plastic is medical grade plastic. In accordance with another aspect of the invention, the shatter proof material is gamma gassed sterilized.

In accordance with still another embodiment of the invention, the bottle is provided with a molded-in eye.

In accordance with another aspect of the invention, the cap defines an internal thread that mates with a thread on the bottle to removably attach the cap to the bottle. In accordance with another aspect of the invention, a seal is provided between the bottle and the cap.

In accordance with another embodiment of the invention, the cap further includes a funnel having a first portion size to be received within the mouth of the bottle and a second portion that extends radially outward from the first portion to define a shoulder that is wider than the mouth of the bottle, where the cap fits over the shoulder and threads onto the bottle to compress the shoulder against the rim of the mouth of the bottle. According to another aspect of the invention, an 0 ring is provided between the shoulder and the rim of the bottle. In accordance with another aspect of the invention, a self-sealing membrane is placed between the cap and the second portion of the funnel, where the self-sealing membrane is trapped between the cap and the funnel when the cap is attached to the bottle. In accordance with another aspect of the invention, the self-sealing membrane has a flexible edge that selectively permits fluid to flow from the bottle to create a vacuum therein. In accordance with another aspect of the invention, the cap when attached to the bottle defines a gap above the self-sealing membrane that permits at least a portion of the self-sealing membrane to move away from the neck of the bottle to permit fluid to flow out of the bottle.

According to another embodiment of the invention, a portable suction assembly is provided including a bottle having a cap assembly mounted thereon, the cap assembly including a self-sealing membrane that covers the opening of the bottle, a cap that fits over the self-sealing membrane and attaches to the bottle to hold the self-sealing membrane over the opening. The cap defining a gap above the self-sealing membrane that allows selective displacement of the self-sealing membrane to draw fluid from the bottle to form a lower pressure than ambient pressure therein, wherein the cap includes an opening that exposes a portion of the self-sealing membrane, and a tubular member having a tip that penetrates the self-sealing membrane to apply suction to the tubular member. According to the method, the end of the tubular member is inserted into a body of fluid using the vacuum within the bottle to draw fluid from the body. According to the method of the invention, wherein the body of fluid includes vehicle or engine fluid such as fuel, coolant, oil, brake fluid, diesel emissions fluid, and refrigerant. According to another aspect of the invention, the body of fluid includes medical fluids including bodily fluids and medical fluids.

According to another embodiment of the invention, a method of creating a vacuum within a bottle via a cap assembly according to the invention is provided. The method includes providing a bottle, inserting a first portion of a funnel into the bottle, where a second portion of the bottle extends outward and upward from the first portion to form a floor, inserting a self-sealing membrane into the second portion of the funnel such that an edge of the self-sealing membrane lies over the floor, and trapping the self-sealing membrane within the funnel by attaching a cap over the second portion of the funnel and attaching it to the bottle. According to another embodiment, the cap when attached to the bottle defines a clearance that allows the self-sealing membrane to flex or move to permit fluid flow between sealing membrane and the shoulder. The method further includes placing the bottle in a chamber applying a negative pressure to flex or move the self-sealing membrane away from the shoulder to draw fluid within the bottle out to form a vacuum within the bottle, and releasing the negative pressure to allow the membrane to contact the shoulder and form a seal. According to another embodiment, the method includes forming one or more openings with the cap that overlie the edge of the self-sealing membrane. The method includes drawing fluid from the bottle through the at least one or more openings.

The invention further provides an evacuated bottle system including providing a bottle defining a hollow interior, the bottle having a neck defining an opening that provides fluid communication with the interior; providing a cap assembly including a funnel having a first portion and a second portion, where the second portion extends radially outward from the first portion to form a floor on an interior thereof and a shoulder on an exterior thereof, the first portion defining a first bore and the second portion defining a second bore fluidly connected to the first bore; a self serum stopper having a self sealing membrane that extends radially outward to overlie at least a portion of the floor of the funnel; and a cap having a cap wall sized to fit over the funnel and a cover portion extending radially inward from the cap wall, the cover portion defining at least one evacuating opening; assembling the cap assembly with the bottle by inserting the first portion of the funnel into the neck of the bottle; supporting the funnel on the neck of the bottle at the shoulder; inserting the serum stopper within the funnel where the self-sealing membrane covers at least a portion of the floor to seal the first bore of the funnel from the second bore; applying the cap over the funnel and attaching the cap to the bottle, wherein the cover portion extends radially inward over a portion of the self-sealing membrane and defines a gap axially outward of the self-sealing membrane; applying a pressure differential relative to the interior of the bottle to create a suction at the evacuating opening to draw the self-sealing membrane axially outward within the gap a distance effective to provide fluid communication between the first bore of the funnel and the second bore the funnel; maintaining the suction until a selected pressure is achieved within the interior of the bottle; and withdrawing the suction, wherein the selected pressure within the bottle draws the self-sealing membrane against the floor of the funnel to reseal the interior of the bottle.

The invention further provides a system for evacuating a bottle including an assembly station wherein a cap assembly is attached to the bottle, the cap assembly including a funnel having a first portion and a second portion, where the second portion extends radially outward from the first portion to form a floor on an interior thereof and a shoulder on an exterior thereof, the first portion defining a first bore and the second portion defining a second bore fluidly connected to the first bore; a serum stopper received in the second bore of the funnel having a self sealing membrane that extends radially outward to cover at least a portion of the floor; and a cap having a cap wall sized to fit over the funnel and a cover portion extending radially inward from the cap wall, wherein the cover portion defines a gap over the self sealing membrane, the cover portion defining at least one evacuating opening located at least partially radially outward of a perimeter of the self sealing membrane; an evacuation station including a head having a port adapted to fluidly communicate with the evacuating opening, the head being in selective fluid communication with a vacuum source to apply a suction to the evacuating opening causing the self sealing membrane to be displaced upward from the floor into the gap to allow fluid communication between the port and the bottle to draw fluid from the bottle.

The following description and the annexed drawings set forth in detail certain illustrative aspects of the claimed subject matter. These aspects are indicative, however, of but a few of the various ways in which the principles of the innovation may be employed and the claimed subject matter is intended to include all such aspects and their equivalents. Other advantages and novel features of the claimed subject matter will become apparent from the following detailed description of the innovation when considered in conjunction with the drawings.

BRIEF DESCRIPTION OF THE DRAWINGS

FIG. 1 is an exploded perspective view of a cap assembly for a bottle according to the invention.

FIG. 2 is a top perspective view of a cap assembly according to the invention.

FIG. 3 is a top perspective view of a serum stopper having a self-sealing membrane according to one embodiment of the invention.

DETAILED DESCRIPTION OF THE INVENTION

Figure 4:
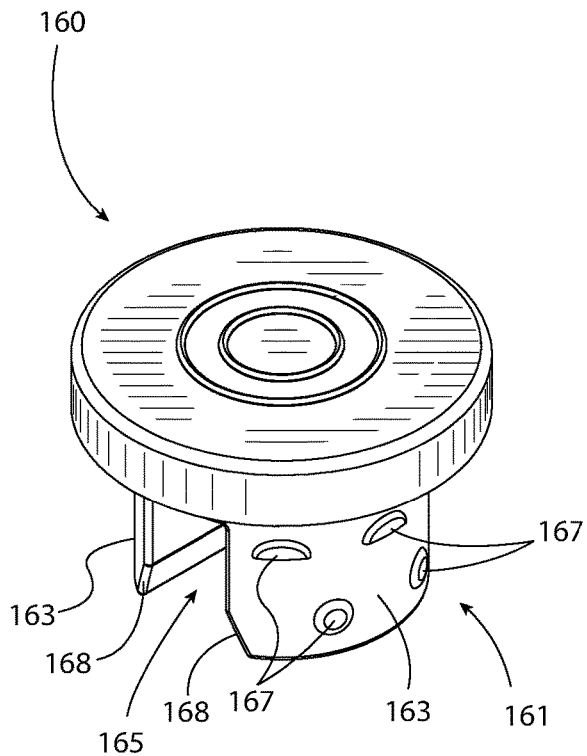
FIG. 4 is a top perspective view of a serum stopper having a self-sealing membrane according to an alternate embodiment of the invention.
Figure 5:
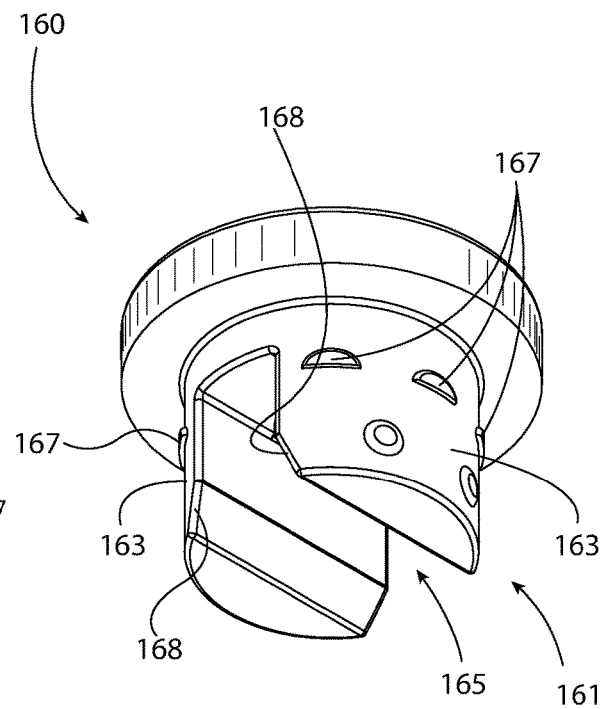
FIG. 5 is a bottom perspective view thereof.
Figure 6:
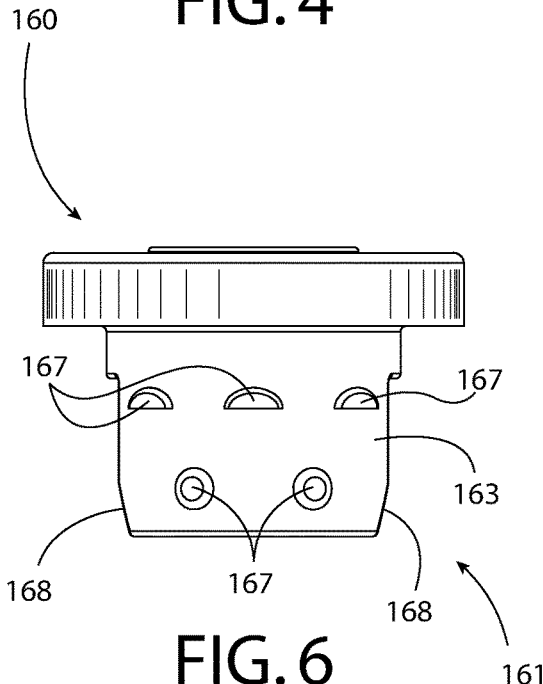
FIG. 6 is a side view thereof.
Figure 7:
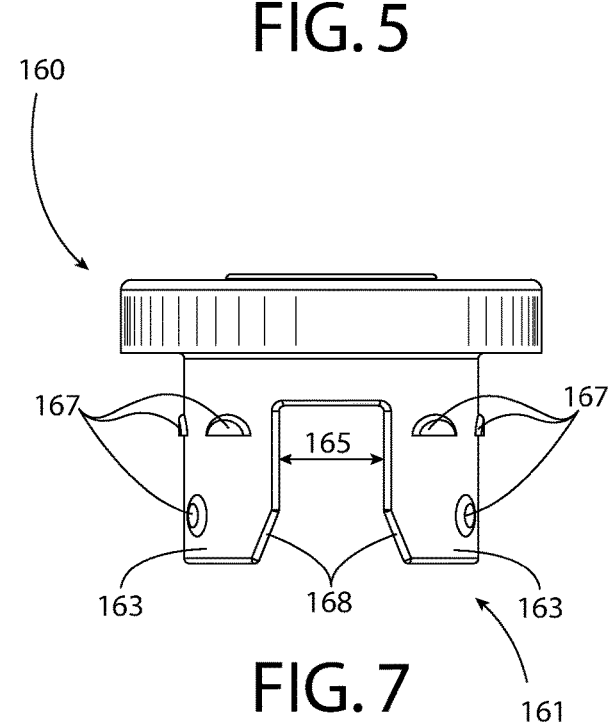
FIG. 7 is a front view thereof.
Figure 8:
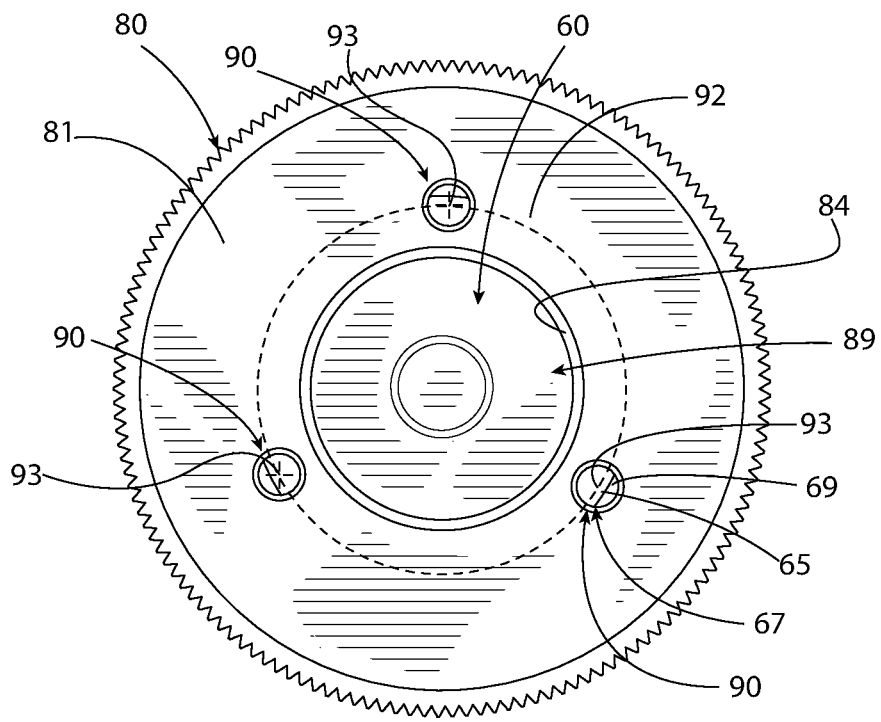
FIG. 8 is a top view of a cap assembly according to the invention.
Figure 9:
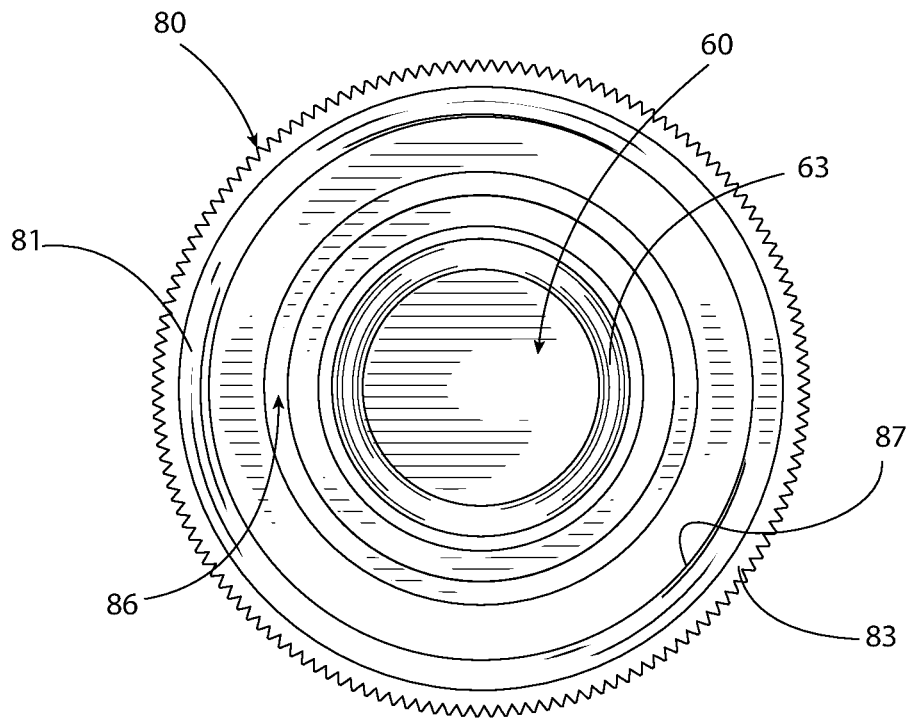
FIG. 9 is a bottom view thereof.
Figure 10:
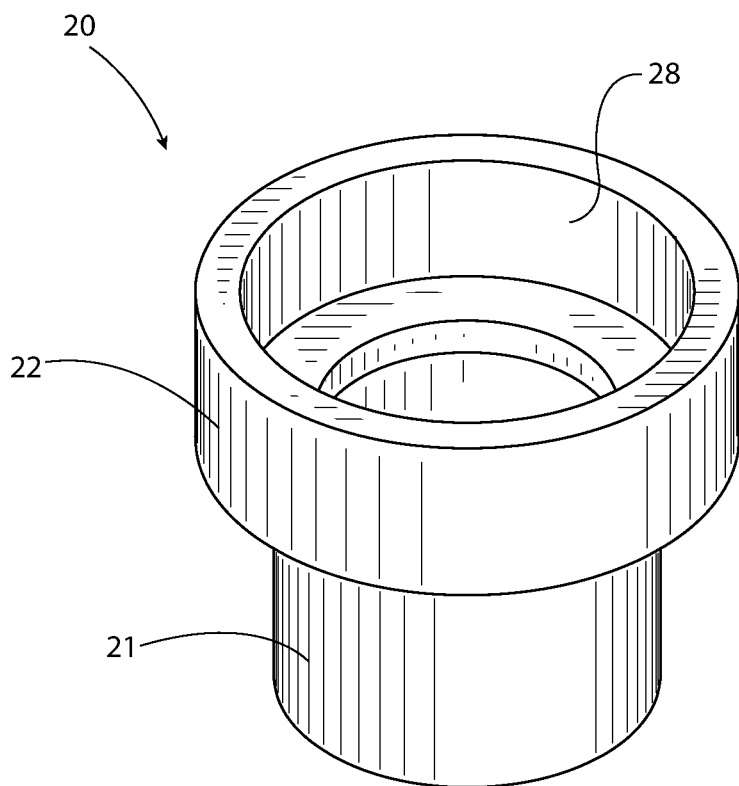
FIG. 10 is a top perspective view of a funnel component according to the invention.
Figure 11:
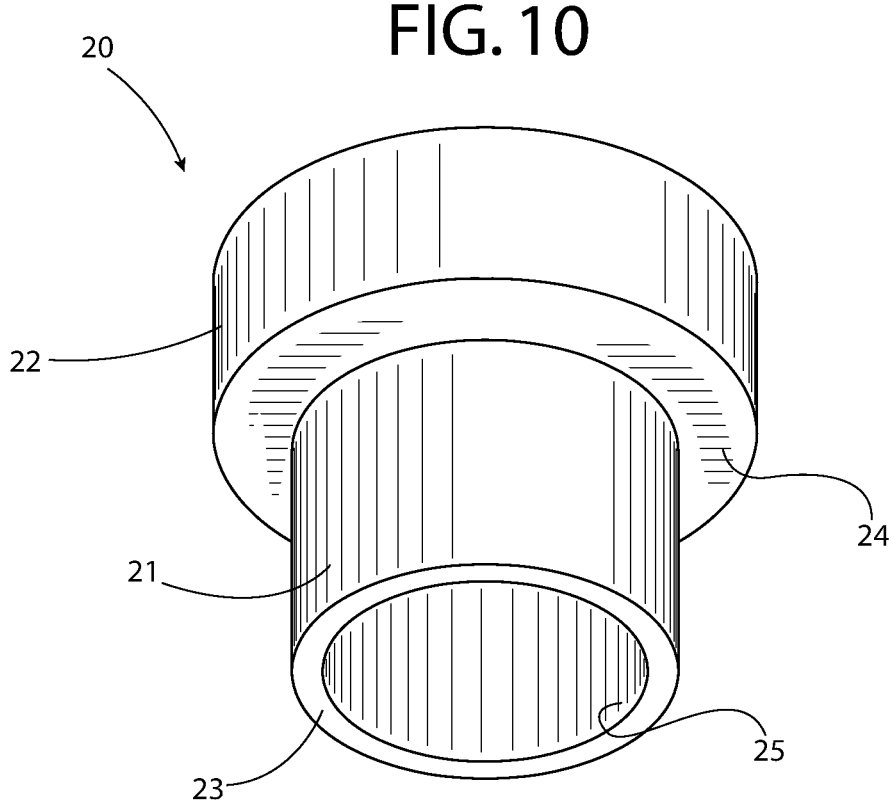
FIG. 11 is a bottom perspective view thereof.
Figure 12:
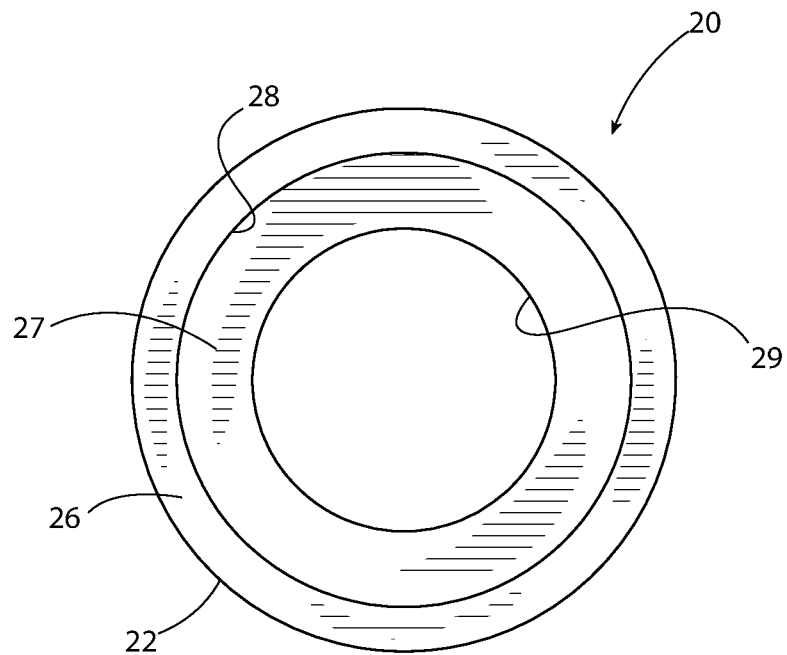
FIG. 12 is a top view thereof.
Figure 13:
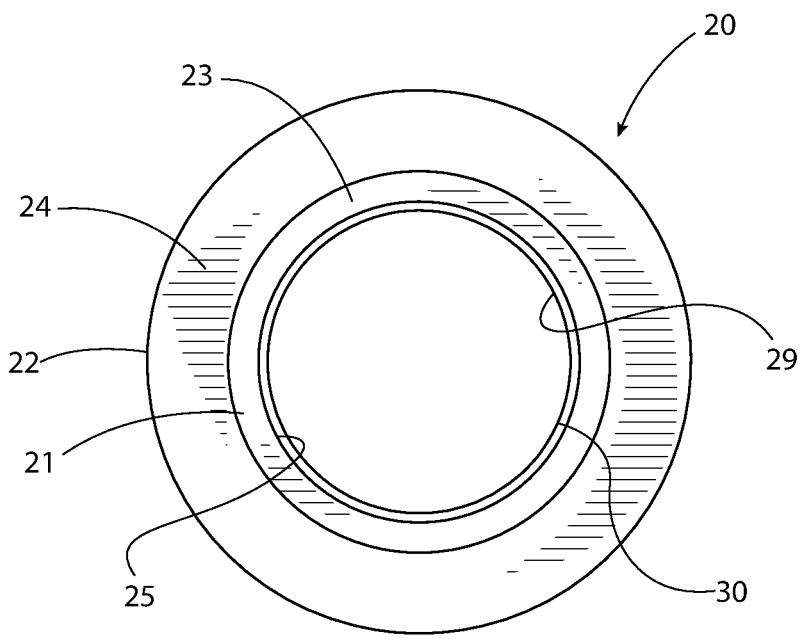
FIG. 13 is a bottom view thereof.
Figure 14:
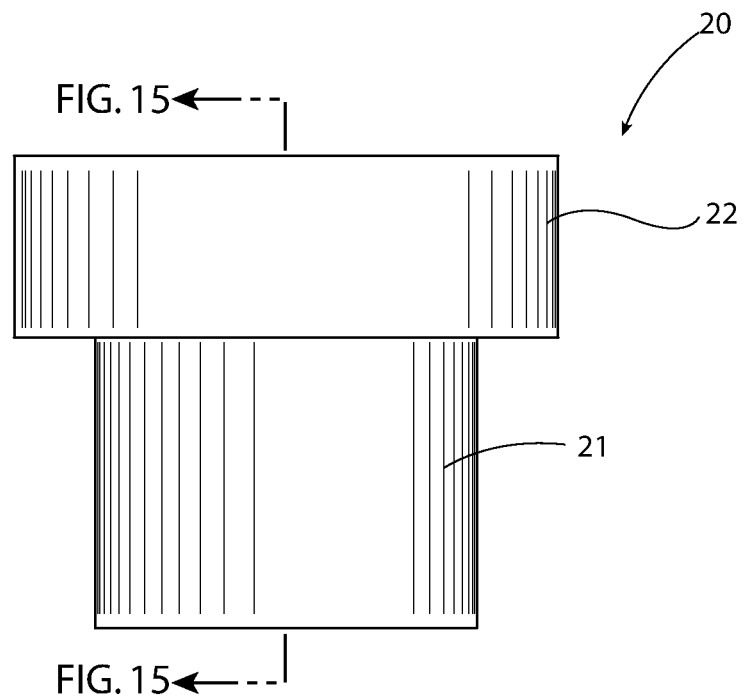
FIG. 14 is a side view thereof.
Figure 15:
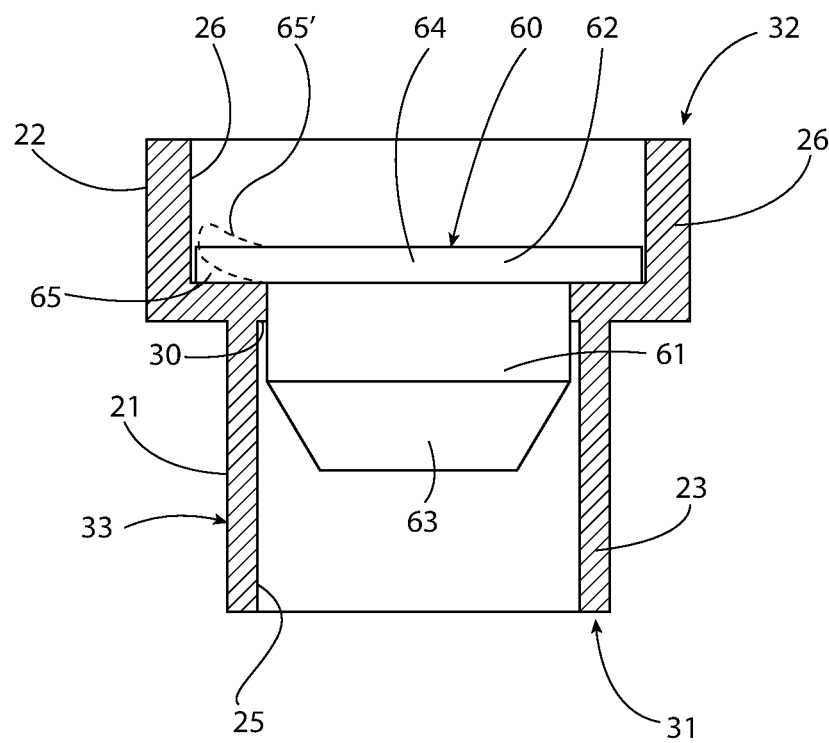
FIG. 15 is a sectional view as might be seen along line 15-15 in FIG. 14.

A cap assembly for a medical bottle according to the invention is generally indicated by the number 10 in the drawings. Cap assembly 10 includes a funnel 20, a self-sealing membrane 60 and a cap 80. Optionally, a seal 50 may be provided between the funnel 20 and bottle B as described more completely below.

With reference to FIG. 1 and FIGS. 10-15, funnel 20 generally includes a first portion 21 and a second portion 22. First portion 21 is sized to be received within the mouth M of bottle B. First portion 21 may have a variety of shapes or configurations suitable for insertion of first portion 21 within an opening or mouth M of bottle B. In the example shown, first portion 21 has a cylindrical configuration including a first wall 23 that defines a first bore 25. Second portion 22 includes a shoulder 24 that extends radially outward from first wall 23 to engage the rim R of bottle B to support second portion 22 above rim R. In the example shown, shoulder 24 extends perpendicular to wall 23 to form a flat shoulder that extends parallel to the upper surface of rim R. It will be understood that other configurations including tapered shoulders may be used to act as a stop and support second portion 22 on rim R. As in the case of first portion 21 a variety of configurations or shapes may be used for the second portion 22 including but not limited to the cylindrical shape shown. In the example shown, second portion 22 includes a second wall 26 that defines a second bore 28 above first bore 25. As shown, second bore 28 may be sized larger than first bore 25 although other configurations including same sized bores 25, 28 or a smaller second bore 28 may be used.

In the example shown, shoulder 24 divides first portion 21 and second portion 22. Shoulder 24 forms a floor 27 and may extend inward of first bore 25 to form a third bore 29 that has a smaller lateral dimension than first bore 25 and second bore 28. In the example shown, a lip 30 is formed above first bore 25. The lip 30 has a relatively small axial dimension compared to the first wall 23 to provide reduced frictional contact with self sealing membrane 60 as discussed more completely below.

As shown, first bore 25, second bore 28 and third bore 29 are in fluid communication with each other and open at each end of funnel 20. In particular, first end 31 of funnel 20 is insertable into the mouth of bottle B and is open to the interior of bottle B. Second end 32 of funnel 20 opens upwardly.

When assembling the cap assembly 10, a seal 50 may be provided between the funnel 20 and bottle B. Seal 50 may be formed integrally with funnel 20 or a separate seal may be provided. Seal 50 may be any suitable sealing member including but not limited to a sealing tape, a gasket, or an o-ring as shown. The seal 50 shown defines a seal bore 52 that is sized to fit around the perimeter 33 of the first portion of funnel 20. Seal 50 loosely conforms to the perimeter 33 of funnel 20 such that the shape of the interior surface 51 of seal 50 may be any of the shapes described with respect to funnel 20 including but not limited to polygonal shapes or the cylindrical shape shown. In the example shown, interior surface 51 defines a circular bore 52. The exterior surface 53 may have any shape as well including but not limited to polygonal, irregular, or cylindrical shapes. The exterior surface 53 is spaced radially outward of the interior surface 51 by a suitable amount to form a seal between funnel 20 and a rim of bottle B. In the example shown, seal 50 is sized to fit beneath shoulder 24 and has a lateral dimension 54 less than or equal to the lateral dimension of shoulder 24 so that seal 50 does not protrude outward of second portion 22 of funnel 20. As discussed more completely below, this facilitates attachment of the overlying cap 80 to the threads of bottle B.

A self-sealing membrane 60 may be provided within the funnel 20 to close the bottle B from atmosphere when the cap assembly 10 is fully assembled. Self-sealing membrane 60 may have any shape or form including but not limited to a disk or other body 64 having a lateral dimension greater than the dimension of first bore 25 of funnel 20. The perimeter 65 of body 64 contacts floor 27. To selectively pump fluid into or out of the bottle B as discussed more completely below, perimeter of body is displaced from the floor 27 to permit the flow of fluid around the perimeter of body and through bore 25 of funnel 20. Displacement of perimeter 65 may be accomplished by moving the body 64 outward from floor 27 i.e. by applying a negative pressure or suction above body 64 to move it away from floor 27. Alternatively, only the perimeter 65 may be displaced for example by flexing the perimeter 65 away from floor 27 as shown for example in FIG. 15 at position 65'.

As shown, self sealing membrane 60 may be provided on a serum stopper. One such serum stopper is depicted in FIG. 3 with an alternate serum stopper depicted in FIGS. 4-7. Serum stoppers are commercially available in a variety of configurations and sizes. Consequently, the examples shown should not be considered limiting. In the examples shown, serum stopper includes a first portion 61 and a second portion 62. First portion 61 is sized to fit within first bore 25 of funnel 20. In the particular example shown, since lip 30 protrudes into first bore, first portion 61 has a lateral dimension that allows it to fit within third bore 29 formed by lip 30. As a result, sealing contact between first portion 61 is made with lip 30. Lip 30 has a smaller axial dimension than first wall 23 and therefore, contact between first portion 61 of self sealing membrane 60 and funnel 20 occurs over a relatively small area reducing the frictional forces when displacing the self sealing membrane 60 outward to unseal the interior I of bottle B, as discussed more completely below.

Second portion 62 includes the body 64. Body 64 includes a perimeter 65 that extends radially outward of first portion 61 to extend over at least a portion of floor 27. In the example shown, second portion has a lateral dimension similar to the lateral dimension of second bore 28 such that it substantially fills the second bore and covers the floor 27. In the example shown, the thickness of first portion 61 is thinner than second portion 62. The thickness of first portion 61 is selected such that perimeter 65 may flex to allow selective fluid communication used to provide or draw fluid from the bottle B. To that end, the thickness may vary based on the choice of material.

First portion 61 may be constructed to facilitate insertion of first portion 61 into first bore 25. For example, first portion 61 may include an end 63 that tapers inward as it extends downward from first portion 61. Alternatively, as shown in FIGS. 4-7, serum stopper may include a first portion 161 that includes a pair of legs 163 extending downward from membrane 160. The legs 163 are separated by a gap 165 that permits fluid to flow from bottle B when membrane 160 is raised from floor 27 during an evacuation process described more completely below. The legs 163 are flexible and may flex inward toward gap 165 to facilitate insertion. To that end legs 163 are constructed of a flexible material and may include an inward taper 168 at their outer extremity to further reduce their thickness at the point of insertion. This reduced thickness also increases the width of gap 163 at the outer extremity. To help retain the serum stopper during the evacuation process, legs 163 may include outward projections 167 extending from the outer surface of legs 163 to engage a wall of funnel 20. Projections 167 may include any suitable projection including continuous projections such as a rib or ridge or discontinuous projections, such as the various nubs or bumps shown in the figures.

In the examples shown, first and second portions are constructed from the same material. It will be understood that the portions may be constructed of different materials as well. The self-sealing membrane is constructed of a material through which a needle, cannula, or other tubular member that creates fluid communication with the bottle is inserted. The material is self-sealing in the sense that when the needle is withdrawn the material closes the opening created by the needle to restore the seal created by the cap assembly closing the bottle to atmosphere. Various plastically deformable materials including but not limited to polymeric materials, natural and synthetic gums, rubber materials and combinations or composites thereof are suitable for this purpose. In the example shown, self-sealing membrane 60 and serum stopper is constructed of a rubber material.

A cap 80 is applied over the funnel 20 and secured to bottle B. Cap generally includes a cover portion 81 and an axially inward extending wall 82. Cover portion 81 extends radially inward from wall 82 over second bore 28 to overlie at least a portion of self-sealing membrane to retain self-sealing membrane 60 within funnel 20. Cap 80 may be attached to the bottle B or funnel to retain self-sealing member 60 within funnel 20. When cap 80 is attached, cover portion defines a gap 85 above self-sealing membrane 60 that permits displacement of the body 64 or perimeter 65 to permit fluid flow around self-sealing membrane 60 as previously discussed. Cap 80 may be attached to bottle B by a fastener, generally indicated at 86 including but not limited to a weld, adhesive, clip, threads, and the like. In the example shown, cap includes an internal thread 87 that mates with an external thread T on bottle B. To that end, cap wall 82 includes an end 83 that extends axially inward of the second portion 22 of funnel 20 i.e. past the shoulder and is provided with an internal thread that mates with the external thread T of bottle B. As shown, end 83 extends sufficiently to mate with thread T and may also include a clearance 88 to accommodate the seal 50 between funnel 20 and neck N.

Cap 80 may have any shape of configuration suitable for at least partially covering the self-sealing membrane 60 to retain self-sealing member within funnel 20. In the example shown, cap has proportions slightly greater than the neck N of bottle B so that it fits over the neck N of bottle B. Likewise, cap 80 is sized to fit over funnel 20 and seal 50. It will be understood that the outer shape of wall 82 may be varied without affecting the function of the cap 80. The shape shown is one example of an aesthetically pleasing shape that may be used. The wall 82 is generally cylindrical in shape but may also have other shapes including polygon shapes, ribbed contours, corrugated shapes, or arbitrary shapes selected by the designer. The interior shape of the wall 82 may vary depending on the form of attachment used. In the example shown, however, since a threaded fastener 86 mates with a thread T on the bottle, the interior proportions of the wall 82 are sized to define a cap bore 83 of similar dimension to the neck of the bottle B.

Figure 17:
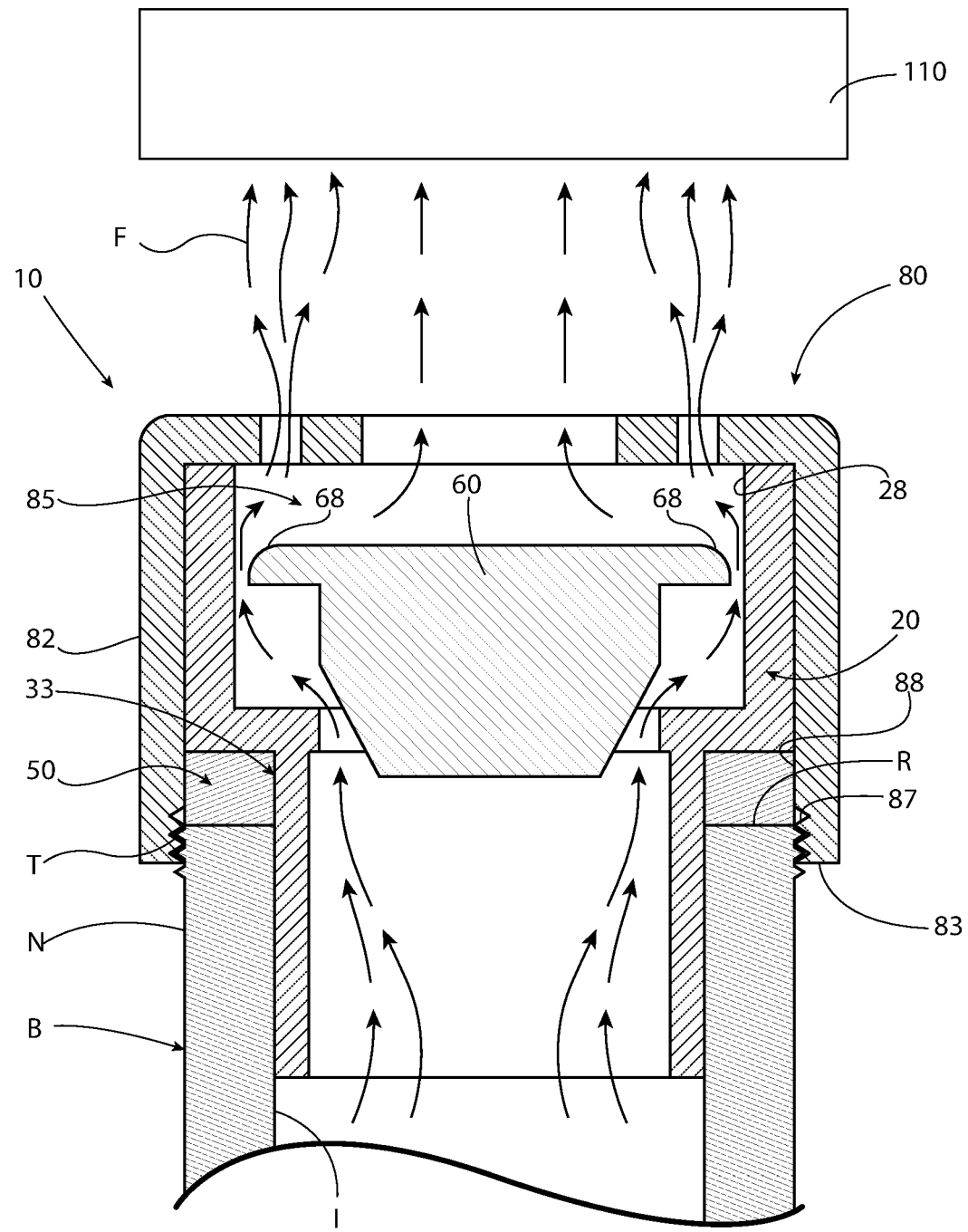
FIG. 17 is an enlarged sectional view of the cap assembly according to the invention showing details of an evacuating operation used to form a lower pressure or vacuum within a bottle on which the cap assembly is installed.

Cover portion 81 of cap 80 may also have any configuration or shape so long as a portion of cover portion 81 extends over self-sealing membrane 60 to retain it. To that end cover portion may include one or more inward extending tabs, walls, or other structures to retain self-sealing membrane 60. In the example shown, cover portion 81 includes an annular wall 84 that defines a central opening 89. The annular wall 84 extends radially inward over the perimeter 65 of body 64 of self-sealing membrane 60. The central opening 89 provides access to self-sealing membrane 60 through cover portion 81 and acts to guide insertion of the needle, cannula or other tubular member. One or more evacuating openings 90 may be provided within cover portion 81 or another portion of cap 80 to facilitate fluid communication within the bottle B as discussed more completely below. The evacuating openings 90 may have any shape or configuration and may be located anywhere on cap wall 82 or cover portion 81. In the example shown, plural evacuating openings 90 are provided on cover portion 81 and located on a common circle 92. The openings 90 each have a circular shape with the center of each opening located on common circle 92. The common circle 92 may generally correspond to and overlies the joint 67 formed between the edge 69 of self-sealing membrane and the wall 28 of funnel 20. In the example shown, common circle 92 is located slightly inward of edge 69 to overlie a portion of perimeter 65. During a filling operation, this location accelerates fluid flow over perimeter 65 near edge 67 of membrane 60 to cause it to move away from funnel 20 or cause perimeter 65 of membrane 60 to flex away from floor 27 to provide fluid communication between the interior of bottle B and atmosphere. When applying a negative pressure to the cap assembly 10, fluid is drawn through evacuating openings 90 and sucks at least the perimeter 65 of membrane 60 away from funnel 20 allowing fluid within the bottle B to be drawn out. In some cases the membrane 60 may be lifted away from floor 27, for example by flexing of perimeter 65 (FIG. 15) or elevation of body 64 as a whole (FIG. 17). This procedure may be used when developing a vacuum within bottle B. To facilitate the flow of fluid into or out of the bottle B, the upper edge 68 of perimeter 65 may be tapered or rounded (FIG. 17). In the example shown, a rounded edge is provided creating a relieved area adjacent to wall 28 of funnel at the upper surface of membrane body 64.

Figure 19:
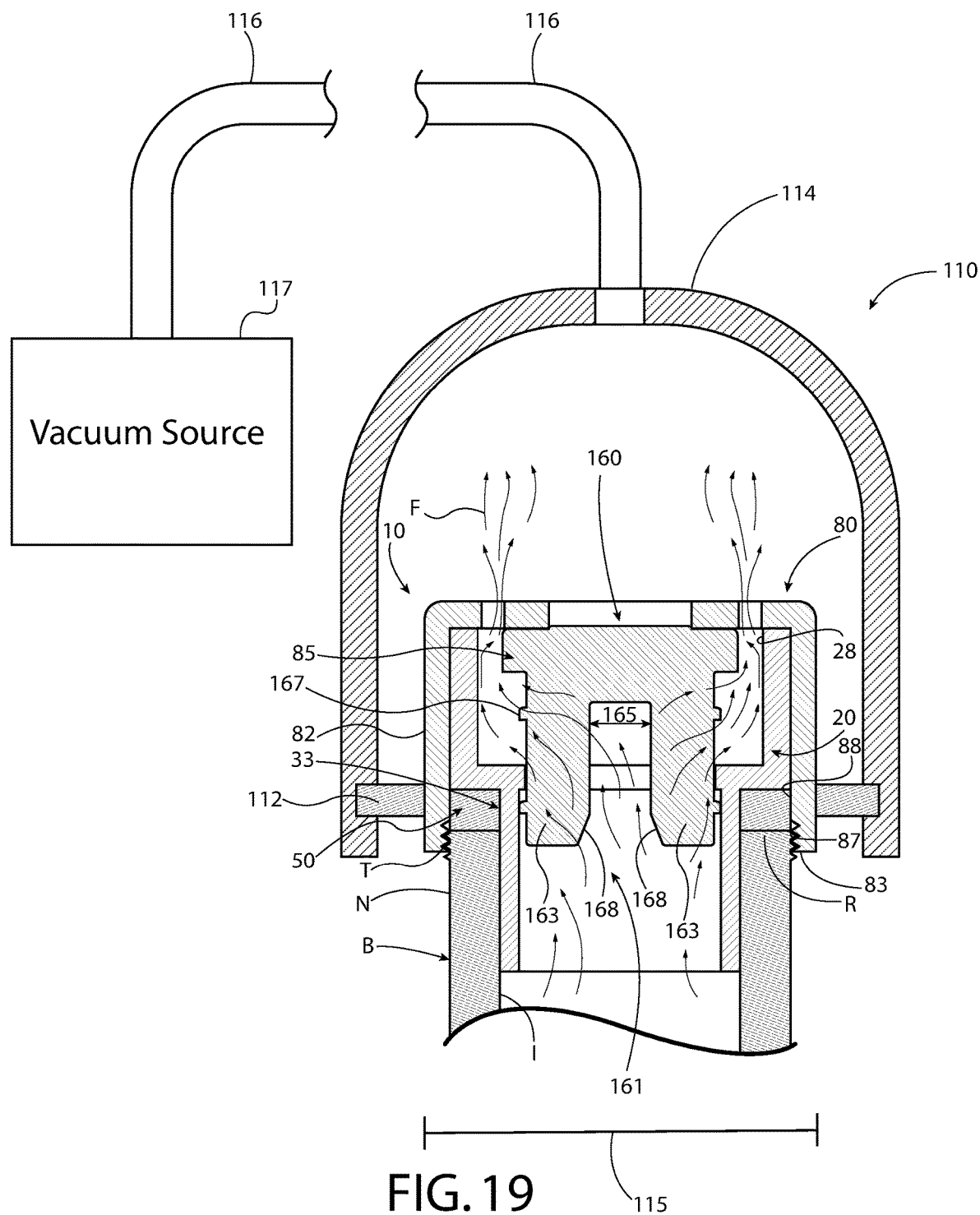
FIG. 19 is an enlarged section view similar to FIG. 17 showing an alternate method of evacuating a bottle and alternate stopper.

According to another aspect of the invention, cap assembly 10 includes a system for forming a vacuum within the bottle B. In its most general form, a self-sealing member is placed over the neck of the bottle to cover the opening formed by the neck. A cap fits over the self-sealing membrane to hold it in place over the opening. The cap is attached to the bottle as discussed above including, for example, by having an internal thread that threads on to an external thread on the neck of the bottle. When the cap is attached, the cap defines a gap above the self-sealing membrane to allow it to be displaced away from the neck of the bottle to allow fluid to be drawn from the bottle. The cap includes one or more openings 90 to which a suction is applied to draw the self-sealing membrane away from the bottle to draw fluid from the bottle and form a vacuum or lower pressure within the bottle. As best shown in FIGS. 17 and 19, the suction applied to form a vacuum or other lower pressure within bottle B acts on membrane 60 to draw it upward within the gap defined by the cap. As shown in FIG. 17, the serum stopper containing the membrane 60 may move upward and be displaced from the funnel 20. In some instances, the suction is sufficient to cause the serum stopper to rise to the point of contacting the cap. In doing so, this may seal the central opening within cap 80. To that end, the openings 90 are spaced radially outward to permit fluid flow through these openings despite contact between the serum stopper and the cap. Membrane 60 may include a rounded perimeter or other contour that facilitates maintenance of fluid flow around the perimeter and through openings 90. As discussed, alternate serum stoppers may be used. The alternate serum stopper shown in FIGS. 5-7 and 19 includes a pair of legs 163 separated by a gap 165. This serum stopper is designed to remain at least partially within the bore of funnel even during suction. To that end, the legs 163 have a length sufficient to remain in the bore 25 of funnel 20 even when membrane 160 engages cap 80 during evacuation. The presence of the gap 165 between legs 163 permits fluid flow from bottle B when the membrane 60 is elevated from floor 27. To help hold serum stopper in bore 25 of funnel 20 and to resist inadvertent displacement of serum stopper, legs may include outward projections 167, such as nubs and the like that engage the inside wall of funnel 20. To facilitate insertion, legs 163 may be made flexible and include an inward taper 168 at their outward extremity to further reduce their thickness and facilitate inward flexion of the legs 163 during insertion.

According to one method of the invention, the suction is applied by providing the bottle B with the cap assembly 10 attached within a chamber 100 that is at a lower pressure $P_1$ than the fluid, which is air in the example shown, within the bottle B such that the air is drawn from the bottle B by displacing at least a portion of the self-sealing membrane away from neck N of the bottle B as discussed above. As the pressure in the bottle $P_2$ equalizes with the pressure in the chamber 100 the pressure differential on the membrane 60 decreases causing the self-sealing membrane 60 to return to the closed configuration to reseal the bottle B. Removing the bottle B from the chamber 100 or pressurizing the chamber 100 so that it has a pressure greater than the pressure within the bottle provides a pressure differential that holds the self-sealing membrane against the neck of the bottle to seal it from the atmosphere. The suction within the bottle may be accessed by the step of inserting a tubular member through the self-sealing membrane.

According to another embodiment, the system includes providing a bottle B, inserting first portion 21 of a funnel 20 into a neck N of the bottle B, where the funnel 20 includes a second portion that extends radially outward from the first portion and rests on the neck N of the bottle B. The first portion 21 and second portion 22 each defining a bore 25, 28 that provide fluid communication between the bottle B and the atmosphere. The second portion 22 of the funnel forms a floor 27 or other surface adjacent to the bore 28. A self-sealing member 60 is provided within the bore in the second portion and has a perimeter that is supported on the floor. A cap 80 fits over the second portion 22 of funnel 20 and self-sealing membrane 60 and attaches to the bottle B. The cap 80 defines a gap 85 above the self-sealing membrane 60 that permits displacement of at least a portion of the self-sealing membrane 60 in an upward direction to permit fluid communication between the bottle interior and the outside atmosphere. According to the invention, the bottle with cap assembly 10 installed is placed in a chamber 100. The pressure $P_1$ in the chamber 100 is less than the pressure $P_2$ within the bottle causing displacement of the self-sealing membrane 60 upward away from floor 27 to draw fluid from the bottle B and form a vacuum therein. To facilitate displacement of the self-sealing membrane, one or more openings may be formed in the end or portion of cap that covers the edge of self-sealing membrane. In the example shown, plural openings 90 are provided on a circle 92 that corresponds to the joint between the membrane 60 and the funnel 20. Fluid F drawn through these openings 90 sucks the perimeter 65 of membrane 60 upward from floor 27 (FIG. 17) or away from the wall 26 of funnel 20 (FIG. 15) to open the first bore 25 to the atmosphere within chamber. In the event that the suction causes self sealing membrane to contact cover portion 81 (FIG. 19) closing the central opening of cap 80, rounded corners 68 provide a clearance at openings 90 to maintain the flow of fluid F from bottle B. The radial outward spacing of openings 90 also may be made such that at least a portion of opening 90 is located radially outward of the perimeter of membrane 60 to permit the fluid flow needed to evacuate the bottle B.

Once the vacuum is formed in the bottle B, the pressure within the chamber 100 may be increased causing the self-sealing membrane 60 to return to its normal position or configuration against floor 27 of funnel 20 to reseal the bottle B. It will be appreciated that the vacuum or pressure differential within the bottle B will also help pull the self-sealing membrane inward to maintain the seal.

In an alternative embodiment, to form a vacuum within the bottle, a pressure coupling or nozzles may be provided over, within, or otherwise in fluid communication with openings 90 in the cover portion 81 of cap 80 to create a negative pressure that draws the perimeter 65 of membrane 60 away from funnel 20 to create fluid communication with the interior I of the bottle B. As shown in FIG. 17, pressure device 110 that is in fluid communication with the cap 80 is used to apply suction to openings 90. In still another embodiment, depicted in FIG. 19, pressure device 110 may sealingly engage cap assembly 10 to better apply suction to cap assembly 10.

In the example shown in FIG. 19, pressure device 110 includes a seal 112 that extends inward to engage cap assembly 10. As shown, pressure device 110 may include a housing 114 that defines an opening or port 115 sized to receive cap assembly 10. This housing 114 is fluidly connected to a vacuum source 117 by a suitable conduit 116 or other source that provides a pressure differential needed to provide the desired pressure within bottle B. Once fluid communication is achieved, the nozzles may continue to draw fluid from the interior I of the bottle B until a suitable pressure or vacuum within the bottle is achieved.

Figure 18:
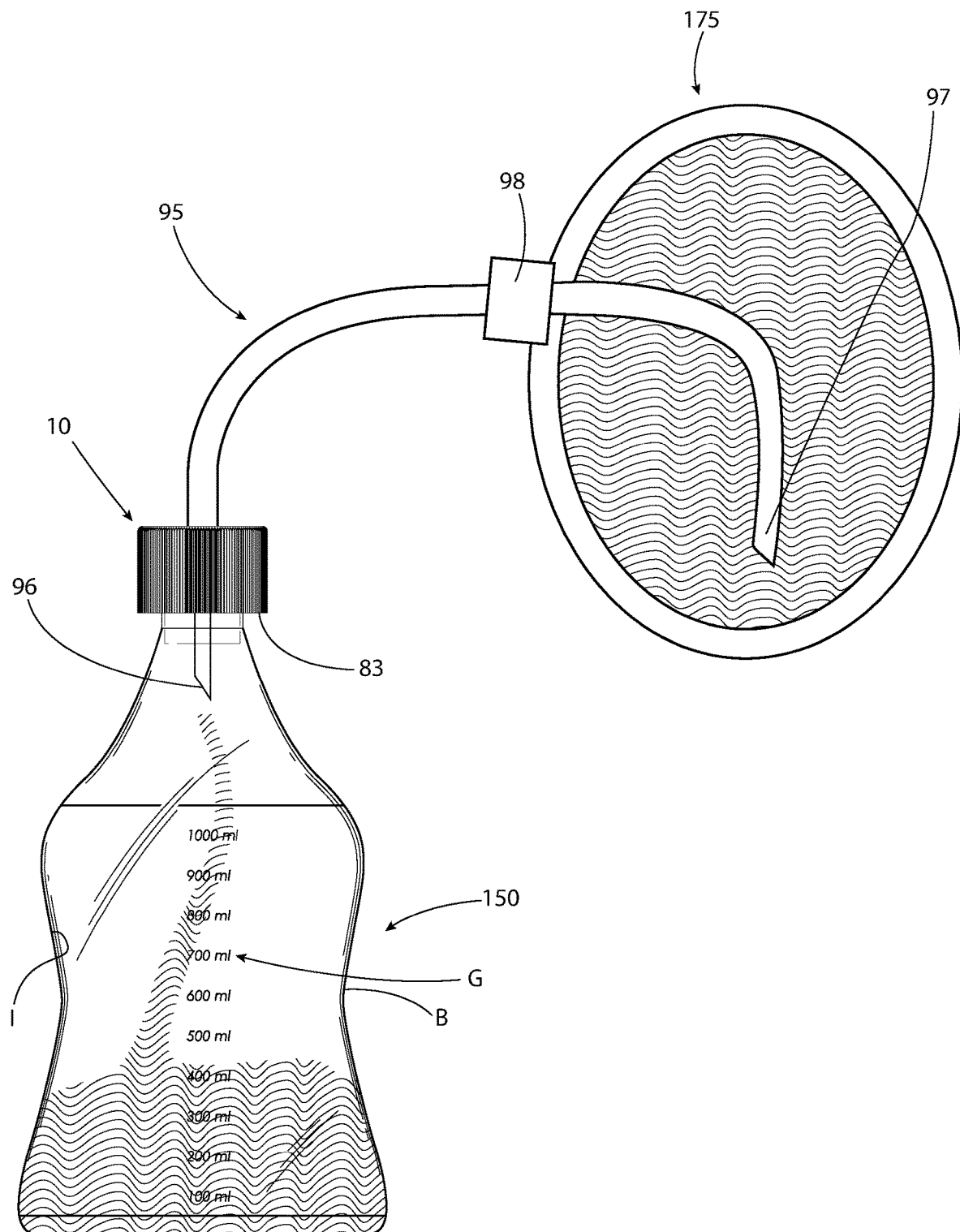
FIG. 18 is a somewhat schematic view of a cap assembly according to the invention used to form a portable suction system to draw fluid from a body of fluid into the bottle.

Once the vacuum or lower pressure is provided within the bottle, the bottle with cap assembly attached may be used as a portable suction device 150 as schematically shown in FIG. 18. The pressure differential provided within the bottle is used to draw fluid into the bottle. To access the suction, a tubular member 95 having a first end or tip 96 capable of penetrating the self-sealing membrane 60 is inserted through the self-sealing membrane 60 and into the lower pressure fluid within the bottle. The opposite end 97 of the tubular member is inserted into a body of fluid, generally indicated at 175 to use the pressure differential between the interior I of bottle B and the body of fluid to draw fluid from the body of fluid into the bottle. As an option, the external end of tubular member may be attached to a variety of attachments to facilitate application of the suction to the body of fluid 175. For example, attachment 98 may include a nozzle, a cap that fits onto a particular container, or a connector that couples the tubular member 95 to a container or other tube.

The portable suction 150 may be applied to any type of fluid 175 including liquids and gases not limited to bodily fluids and other medical application fluids, vehicle or engine fluids including but not limited to fuel, coolant, brake fluid, diesel emissions fluid, and refrigerant.

The bottle B may be of any size or shape and constructed of any suitable material including glass, metal, or plastic. The bottle may be constructed of an opaque, translucent, or transparent material. According to one aspect of the invention, the bottle is constructed of a shatter proof material, but this is not necessary in every application. For example a shatter proof plastic may be used. According to another aspect of the invention, the bottle is constructed of a medical grade shatter proof plastic that has been gamma gas sterilized for use in a medical setting. The bottle may be sterilized according to other known methods for use in a medical setting. In the example shown, the bottle B defines a hollow interior I capable of holding up to 1000 ml of fluid and includes a scale or gradations G visible on the bottle B to aid the user in measuring the amount of fluid in bottle B. The gradations G may be formed on the bottle as by embossing or molding or applied to the bottle B in a subsequent printing or similar process.

Figure 20:
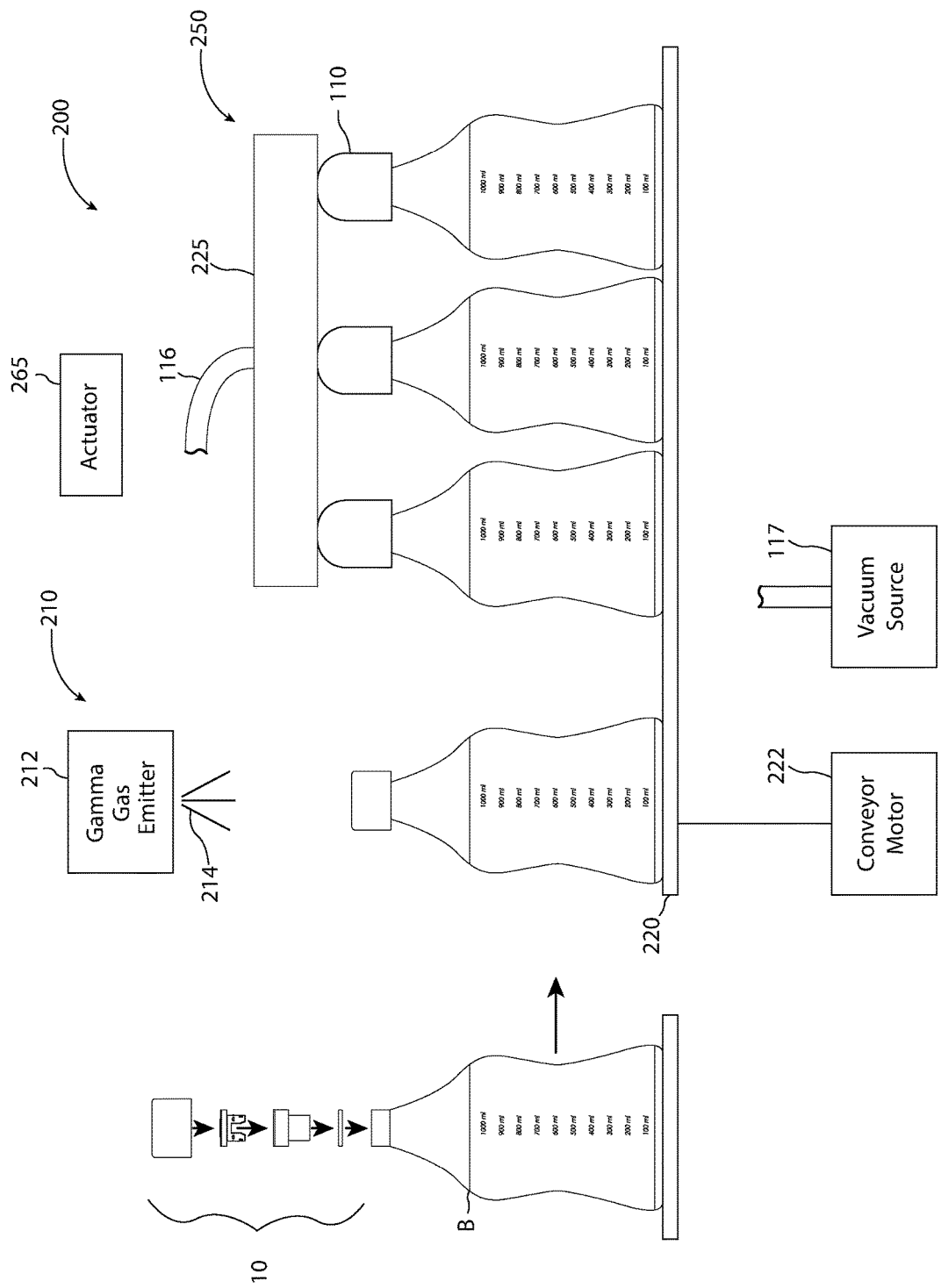
FIG. 20 is a partially schematic view of an automated process for evacuating bottles according to the invention.

According to another embodiment of the invention, the system includes a method of evacuating a bottle in an automated fashion. The method includes installing a cap assembly 10 according to the invention on the bottle B. For example as shown in FIG. 20, cap assembly 10 may include a funnel 20 having a first portion 21 that is inserted within the neck of the bottle B. A seal 50 may be provided between the funnel and the neck and compressed between a shoulder of the funnel and the upper surface of the neck. A self sealing membrane 60 is inserted within the funnel. The sealing membrane 60 rests on a floor 27 within funnel to close the funnel 20 to fluid flow. A cap 80 fits over the funnel 20 enclosing the self sealing membrane therein. Cap 80 may be attached to the bottle B in any manner including an internal thread that mates with an external thread on the neck of the bottle B. In the example shown, attachment of the cap 80 to bottle B compresses seal 50 between the shoulder and the neck causing the outer surface 53 of seal to engage a sidewall 82 of cap 80 and form a seal between the cap 80 and the bottle B.

With the cap 80 secured, a gap 89 is provided between the self sealing membrane and the cover portion 81 of cap 80. This gap permits upward movement of the self sealing membrane 60 when suction is applied to the cap 80. This upward movement displaces self sealing membrane 60 away from floor 27 opening funnel 20 and allowing fluid to flow from bottle B through funnel 20 and out of openings 90 within cap 80. As discussed more completely below, evacuating fluid from the bottle B may be used to create a relatively low pressure within the bottle B. When the suction is removed, the pressure differential created sucks the self sealing membrane 60 against floor 27 resealing the bottle B.

Returning to FIG. 20, system may include an assembly station, generally indicated at 200 where the cap assembly is attached to bottle B. While only a single bottle B is shown at this station 200, it will be understood that multiple cap assemblies may be applied to multiple bottles simultaneously at one assembly station 200. Optionally, cap assembly station 200 may include a disinfecting or sanitizing assembly, generally indicated at 210 to disinfect or sanitize the bottle B and/or cap assembly 10. In the example shown, sanitizing assembly 210 includes a gamma gas emitter 212 that directs sanitizing gamma gas 214 toward the bottle B and cap assembly 10. It will be understood that disinfecting or sanitizing may occur upstream or downstream of the cap assembly station 200 as well.

Once the cap assembly is attached, a conveyor 220 may be used to transport the bottle B to an evacuation station 250. Conveyor 220 may be any system suitable for transporting one or more bottles B to the evacuation station 250 including but not limited to a conveyor belt, a sliding platform, a robot arm, air table, chute, and the like. A drive assembly is provided to provide a motive force a may include an actuator motor, air pump, or a conveyor motor 222 as shown. Drive assembly is operatively connected to the conveyor 220.

Figure 16:
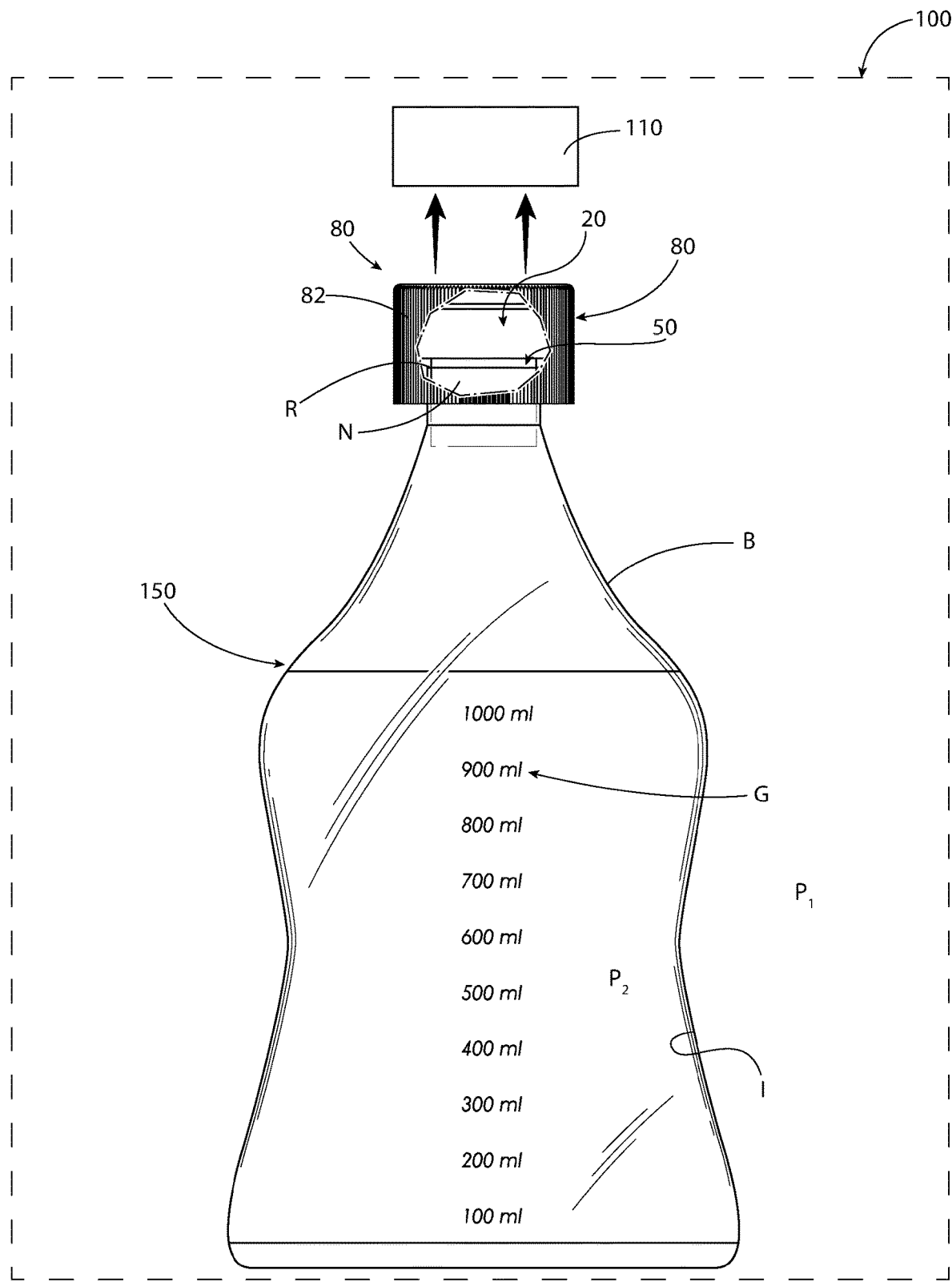
FIG. 16 is a side view of a cap assembly according to the invention mounted on a medical bottle with a portion of the cap cutaway.

The evacuation station 250 generally includes a pressure device 110 as described previously that engages the cap assembly 10 and applies a suction to evacuate fluid from bottle B. To that end, pressure device 110 is connected to a vacuum source 117, which is any pressurizing assembly that can generate a relatively lower pressure within bottle B. Pressurizing assembly may include a pump, vacuum tank, or other assembly that contains or creates a lower pressure or is able to draw fluid from the bottle B. Indeed, as discussed, pressure device 110 may include a chamber 100 (FIG. 16) that is maintained at a lower pressure than the contents of bottle B. As shown in FIG. 19, pressure device 110 may include a single device that engages one bottle B at a time, or, as shown in FIG. 20, pressure device 110 may include a head 255 that fluidly connects to multiple bottles B simultaneously. The head 255 may be moved into fluid communication with the multiple bottles by an actuator 265. Actuator 265 may be any device or combination of devices that moves the head 255 into fluid communication including but not limited to a four bar linkage assembly, linear actuator, or piston assembly (as shown). In the example shown, actuator 265 moves the head 255 vertically between a first position where the head 255 is spaced from the top surface of the cap assemblies on the bottles B to provide clearance for loading the bottles in the evacuation station, and a second position where the ports 115 within head 255 fluidly connect to the cap assemblies 10 of bottles B.

Head 255 includes multiple ports 115 that each engage a single cap assembly 10. A single conduit 116 may provide suction to each port 115 through a manifold. For example, head 255 may include a 3×3 array of ports 115 such that 9 bottles may be evacuated simultaneously. This number is purely an example and is not limiting as head 255 may have any number of ports 115 in any arrangement for evacuating one or more bottles B. After evacuation, the bottle B may be transported downstream of evacuation station 250 for further processing or ejected to a packing station.

While principles and modes of operation have been explained and illustrated with regard to particular embodiments, it must be understood that this may be practiced otherwise than as specifically explained and illustrated without departing from its spirit or scope.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

Specific embodiments of an innovation are disclosed herein. One of ordinary skill in the art will readily recognize that the innovation may have other applications in other environments. In fact, many embodiments and implementations are possible. The following claims are in no way intended to limit the scope of the subject innovation to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means".

Although the subject innovation has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (e.g., enclosures, sides, components, assemblies, etc.), the terms (including a reference to a "means") used to describe such elements are intended to correspond, unless otherwise indicated, to any element which performs the specified function of the described element (e.g., that is functionally equivalent), even though not structurally equivalent to the disclosed structure which performs the function in the herein illustrated exemplary embodiment or embodiments of the innovation. In addition, while a particular feature of the innovation may have been described above with respect to only one or more of several illustrated embodiments, such feature may be combined with one or more other features of the other embodiments, as may be desired and advantageous for any given or particular application. Although certain embodiments have been shown and described, it is understood that equivalents and modifications falling within the scope of the appended claims will occur to others who are skilled in the art upon the reading and understanding of this specification.

It is to be appreciated that the bottle and cap assembly as described herein can be manufactured and produced with recyclable materials. Moreover, the bottle and/or the cap assembly described herein can be reused after cleaning, sanitizing, and/or sterilization. For instance, a bottle and cap assembly can be used for housing and/or disposing a liquid and such bottle and cap assembly can be at least one of cleaned, washed, sanitized, sterilized, and the like to be available for an addition use for housing and/or disposing an additional liquid.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A cap assembly comprising:
    a funnel having a first portion and a second portion,
        the first portion sized to be received within the mouth of a bottle and including a first wall defining a first bore, and
        the second portion including a floor extending radially outward from the first portion to form a shoulder, a second wall extending upward from the floor defining a second bore;

a self-sealing membrane having a perimeter that overlaps at least a portion of the floor; and a cap comprising a cover portion that includes an annular wall that defines a central opening, and at least one evacuating opening located radially outward of the central opening, the cover portion defining a gap above the self-sealing membrane to allow the self-sealing membrane to be at least partially displaced from the portion of the floor to allow fluid communication between the first bore and an outside atmosphere when a suction is applied to the cap.

2. The cap assembly of claim 1, wherein the cap further comprises a cap wall including internal threading.

3. The cap assembly of claim 1, wherein the cover portion defines three evacuating openings circumferentially spaced from each other and located on a common circle, wherein the common circle overlies the perimeter of the self-sealing membrane.

4. The cap assembly of claim 1, wherein the self-sealing membrane comprises:
   a first portion being insertably received in the first bore of the funnel; and
   a second portion extending radially outward relative to the first portion and residing in the second bore of the funnel.

5. The cap assembly of claim 4, wherein the first portion of the self-sealing membrane includes a pair of legs spaced from each other by a gap.

6. The cap assembly of claim 1, wherein the floor extends radially inward to overlap a portion of the first bore of the funnel.

7. The cap assembly of claim 1, further comprising a seal sized to fit around a perimeter of the first portion of the funnel.

8. The cap assembly of claim 1, wherein the at least one evacuating opening is located over or outside of at least a portion of a perimeter of the self-sealing membrane.

9. A cap assembly comprising:
   a funnel having a first portion and a second portion,
      the first portion sized to be received within a mouth of a bottle and including a first wall defining a first bore, and
      the second portion including a floor extending radially outward from the first portion to form a shoulder and a second wall extending upward from the floor defining a second bore;
   a serum stopper comprising:
      a first portion being insertably received in the first bore of the funnel; and
      a second portion comprising a self-sealing membrane, the second portion extending radially outward relative to the first portion and having a perimeter that overlaps at least a portion of the floor and residing in the second bore of the funnel; and
   a cap configured to be secured over the second portion of the funnel such that a gap is defined above the second portion of the serum stopper to allow at least the perimeter of the second portion of the serum stopper to be at least partially displaced from the floor and the first portion of the serum stopper to be at least partially displaced from the first bore of the funnel, wherein the cap assembly is configured to selectively allow fluid communication between an outside atmosphere, the first bore of the funnel, and the second bore of the funnel when a suction is applied to the cap.

10. The cap assembly of claim 9, wherein the cap further comprises a cap wall including internal threading.

11. The cap assembly of claim 9, wherein the cap includes at least one evacuating opening to allow the fluid communication.

12. The bottle assembly of claim 11, wherein the at least one evacuating opening is located over or outside of at least a portion of a perimeter of the self-sealing membrane.

13. The cap assembly of claim 11, wherein the cap includes three evacuating openings circumferentially spaced from each other and located on a common circle.

14. The cap assembly of claim 13, wherein the common circle overlies the perimeter of the self-sealing membrane.

15. The cap assembly of claim 9, wherein the first portion of the serum stopper includes a pair of legs spaced from each other by a gap.

16. The cap assembly of claim 9, wherein the floor extends radially inward to overlap a portion of the first bore of the funnel.

17. A cap assembly comprising:
   a funnel having a first end and a second end, wherein the funnel is configured to be inserted within the neck of a bottle;
   a serum stopper configured to sit at a first position within the funnel,
   the serum stopper comprising:
      a first portion being insertably received in the first end of the funnel; and
      a second portion comprising a self-sealing membrane, the second portion extending radially outward relative to the first portion and residing in the second end of the funnel; and
   a cap configured to be secured over the funnel, wherein the cap includes a cover portion, the cover portion defining a gap above the second portion of the serum stopper to allow both the first portion and the second portion of the serum stopper to be at least partially displaced from the first position within the funnel, and wherein the cap assembly is configured to selectively allow fluid communication between the first end of the funnel and the second end of the funnel when a suction is applied to the cap.

18. The cap assembly of claim 17, wherein the cover portion includes at least one evacuating opening to allow the fluid communication when the suction is applied to the cap.

* * * * *